United States Patent [19]

Fagan et al.

[11] Patent Number: 5,249,864
[45] Date of Patent: Oct. 5, 1993

[54] SYSTEM FOR CHARACTERIZING TEMPERATURE OF FLUIDS

[75] Inventors: John E. Fagan; Ronnie B. Beason, both of Norman, Okla.

[73] Assignee: Gas Research Institute, Chicago, Ill.

[21] Appl. No.: 965,838

[22] Filed: Oct. 23, 1992

[51] Int. Cl.⁵ .................. G01K 1/14; G01K 7/22; G01K 13/02
[52] U.S. Cl. ................................ 374/110; 374/147
[58] Field of Search ................. 374/110, 147, 208

[56] References Cited

U.S. PATENT DOCUMENTS

| | | | |
|---|---|---|---|
| 3,797,310 | 3/1974 | Babcock et al. | 374/110 |
| 4,527,908 | 7/1985 | Arisi | 374/147 |
| 5,172,979 | 12/1992 | Barkley et al. | 374/147 |

FOREIGN PATENT DOCUMENTS

| | | | |
|---|---|---|---|
| 0661633 | 6/1938 | Fed. Rep. of Germany | 374/110 |
| 1466578 | 1/1967 | France | 374/110 |
| 0149025 | 11/1980 | Japan | 374/147 |

OTHER PUBLICATIONS

J. W. Berthold, W. L. Ghering, and D. Varshneya, "Design and Characterization of a High Temperature Fiber-Optic Pressure Transducer", *Journal of Lightwave Technology*, vol. LT-5, No. 7, Jul. 1987, pp. 870–875.

*Primary Examiner*—William A. Cuchlinski, Jr.
*Assistant Examiner*—Diego F. F. Gutierrez
*Attorney, Agent, or Firm*—Dunlap Codding Lee

[57] ABSTRACT

A system for characterizing the pressure, temperature, movement and flow patterns of a fluid under high pressure within a test cell. The test cell is lined internally with adjustable rock facings. Pressure is measured within the test cell using a device employing pressure-distortable optical fibers. Fluid velocity, flow direction, and filter-cake buildup are measured with laser Doppler velocimetry. The flow pattern of the fluid is viewed using corresponding arrays of transmitting and receiving optical fibers. Temperature of the fluid is estimated using a combination of thermal sensors. The pressure, velocity, viewing and temperature systems are integral to the rock facings of the test cell.

8 Claims, 10 Drawing Sheets

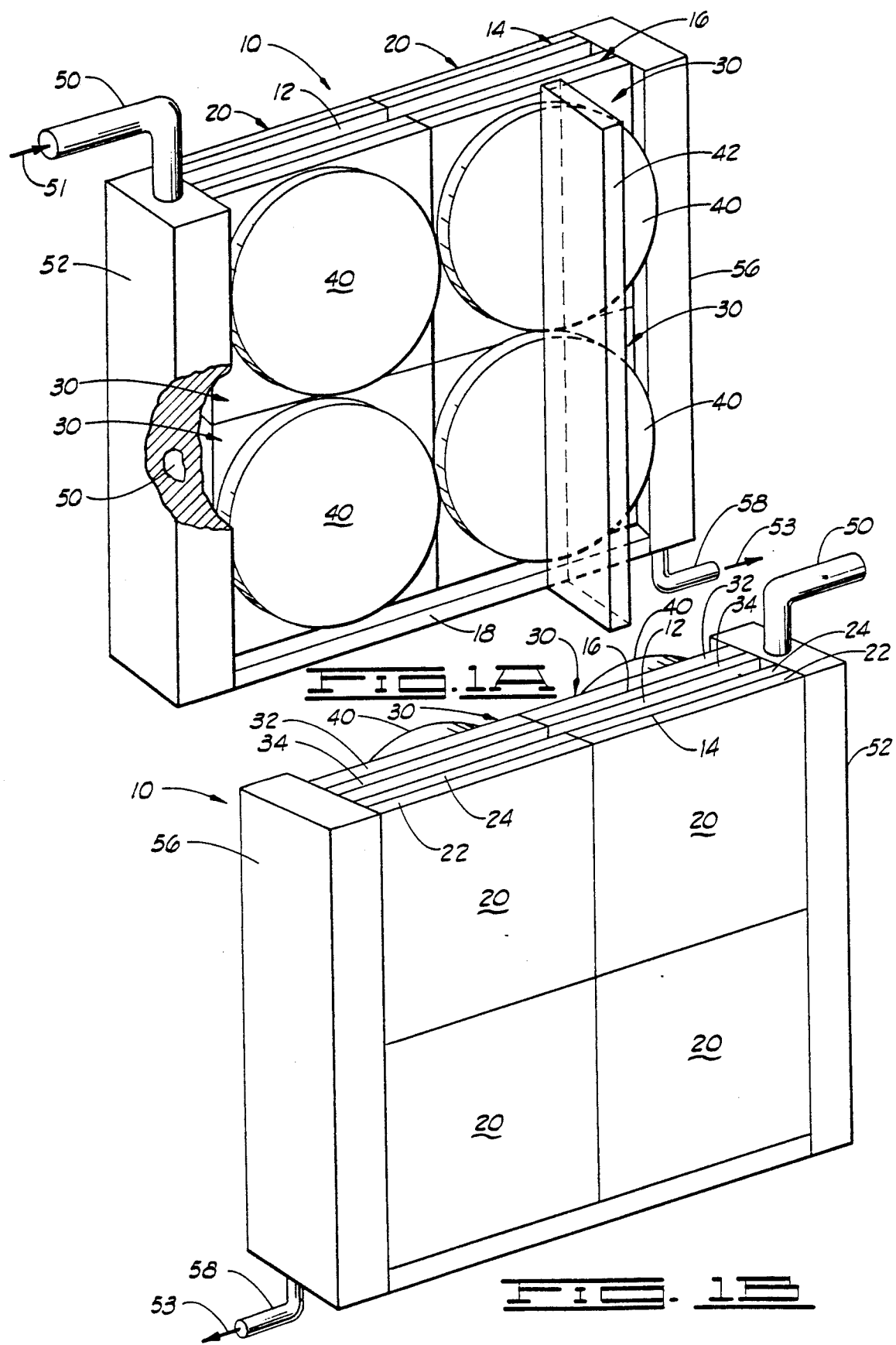

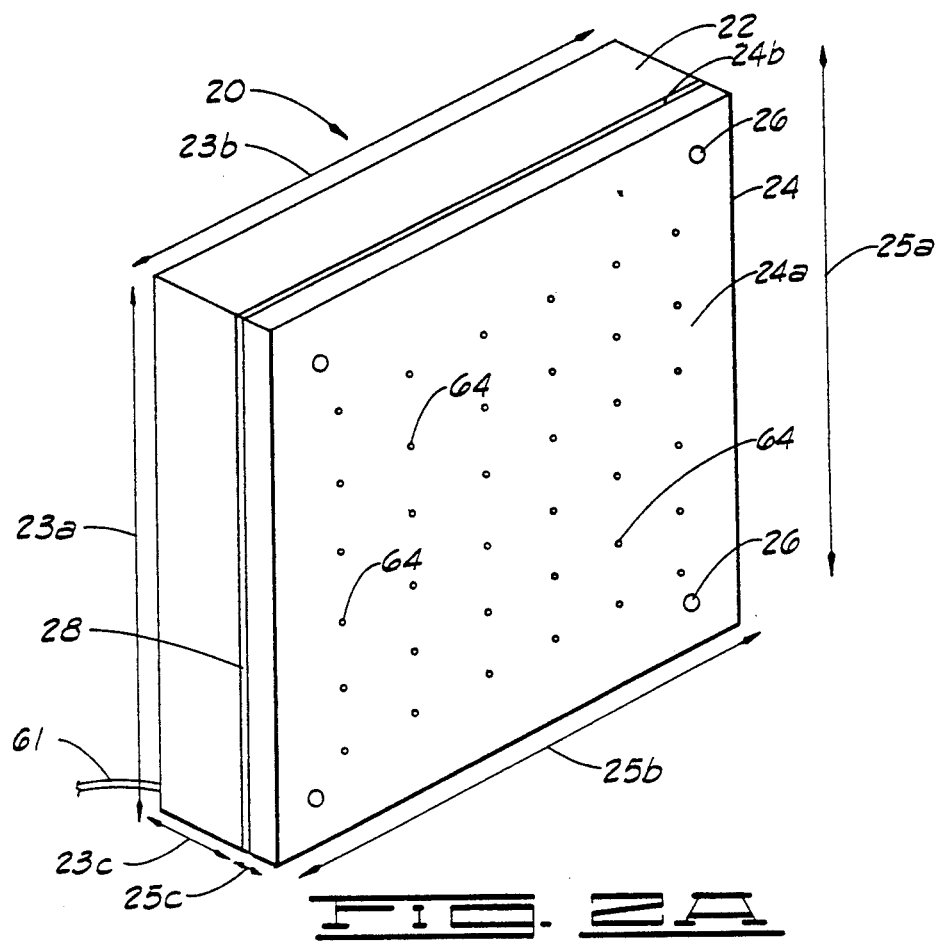
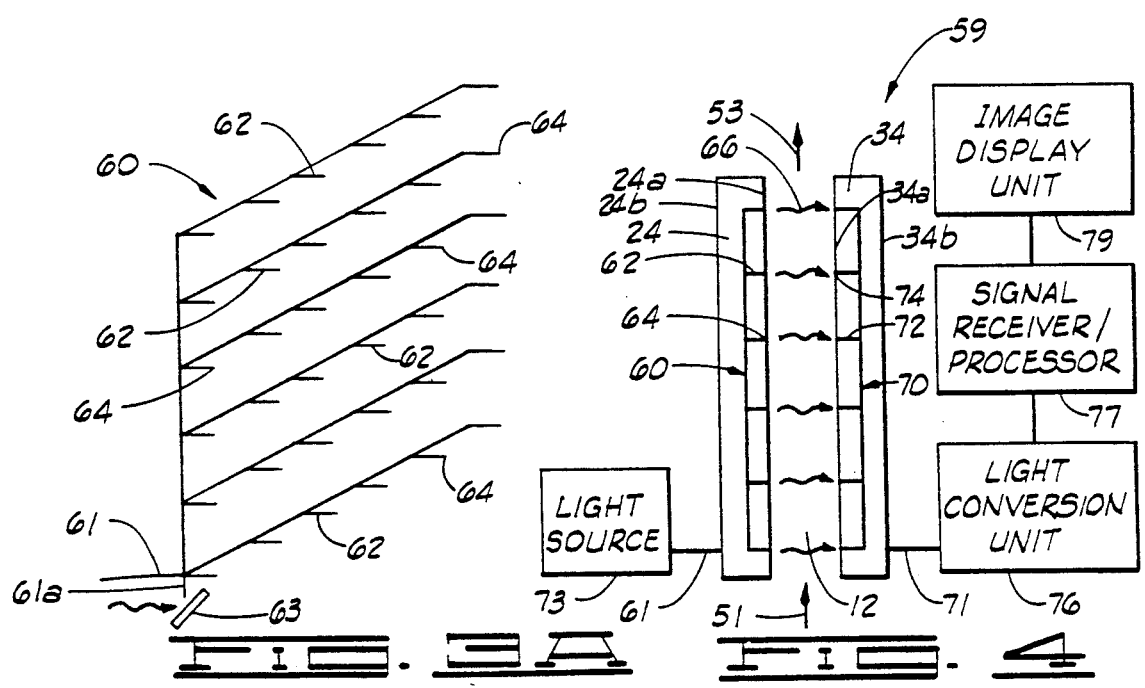

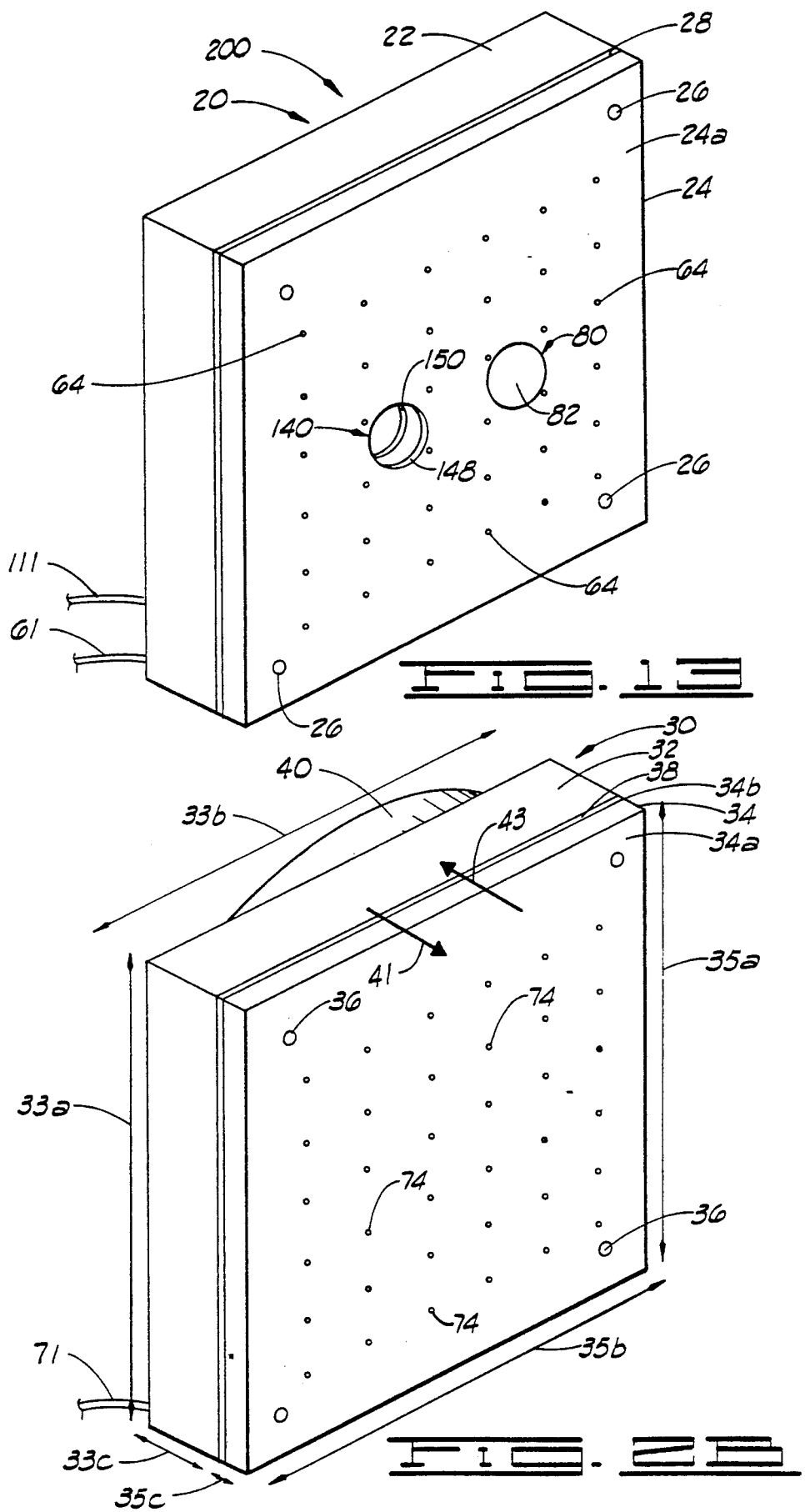

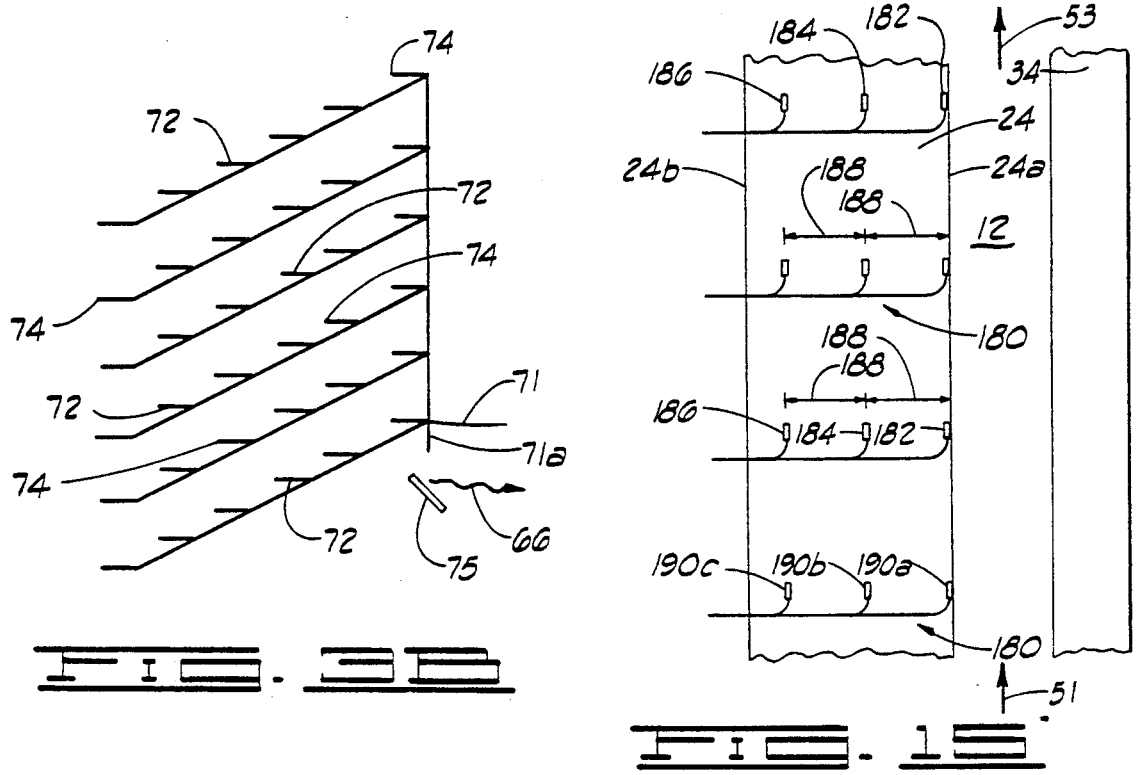
FIG. 3B
FIG. 15
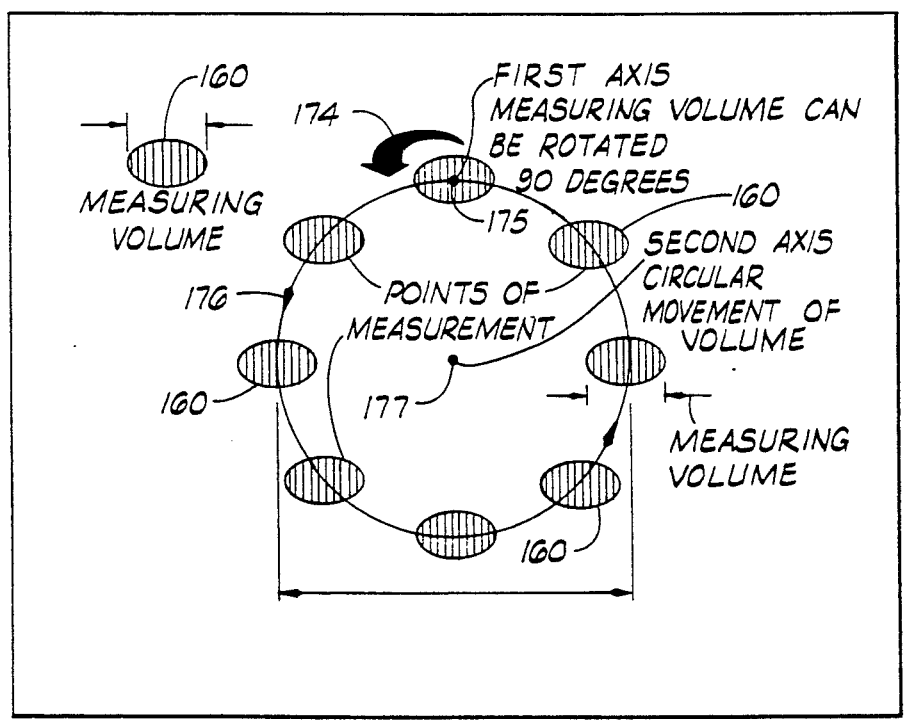
FIG. 14

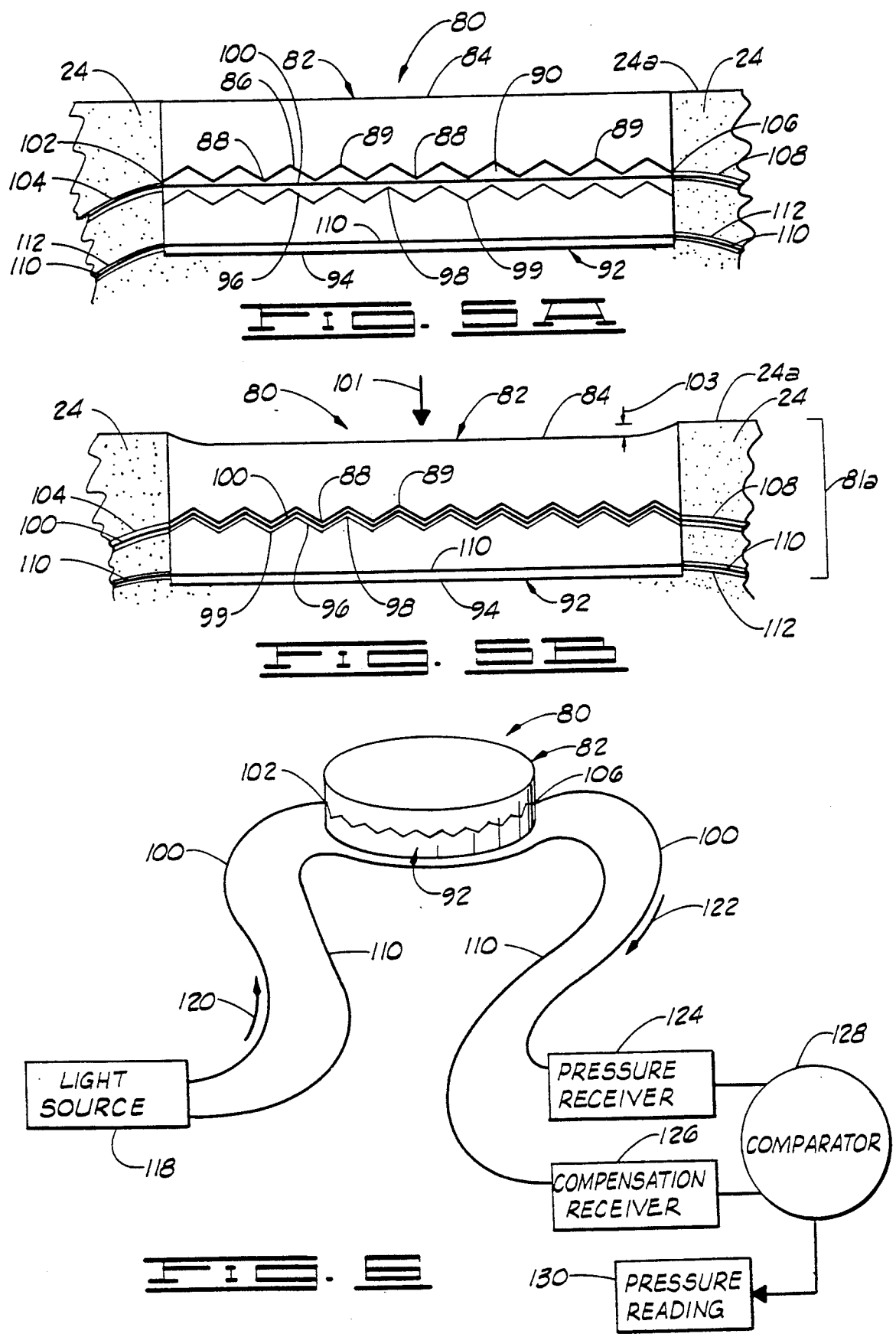

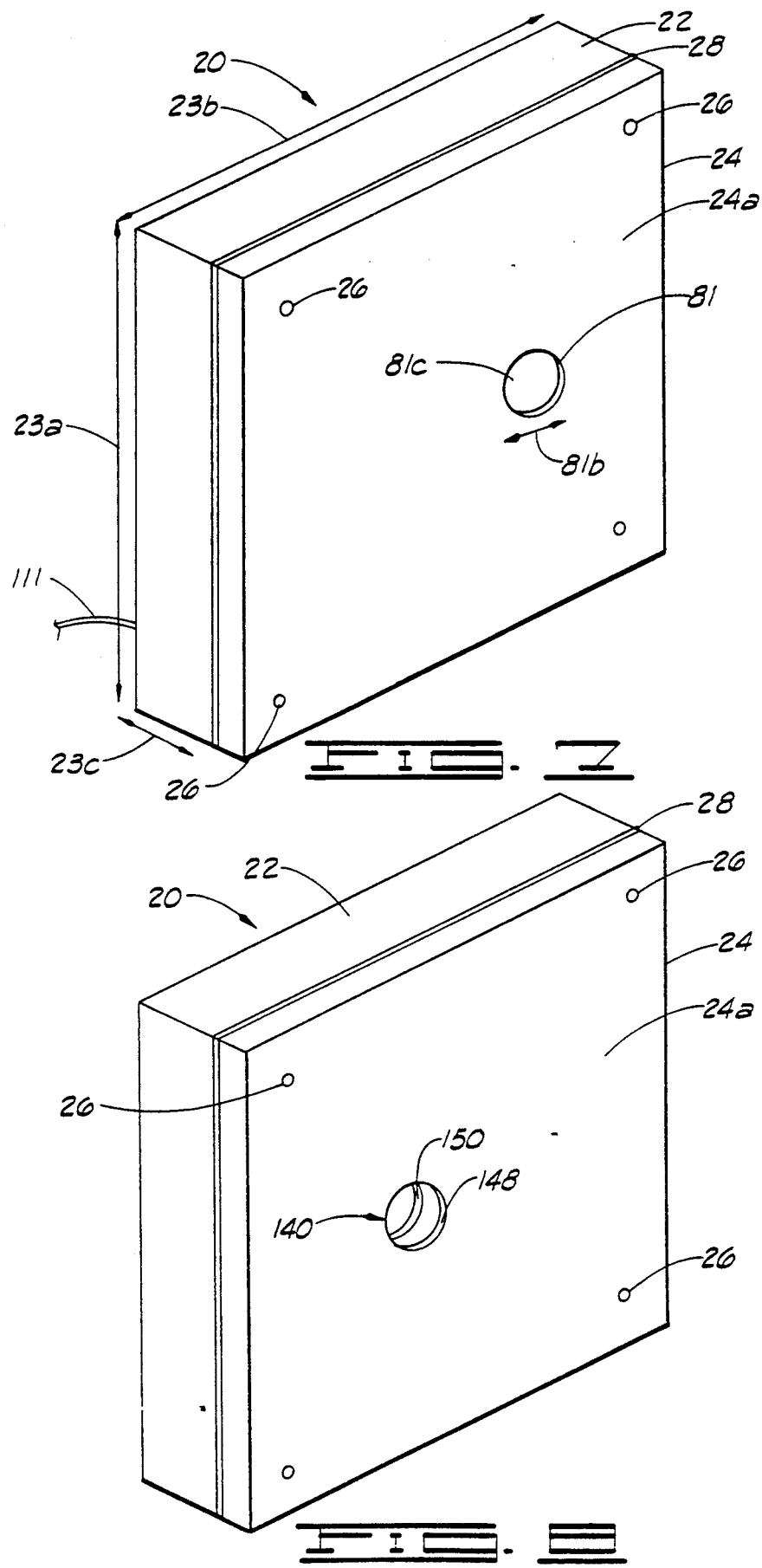

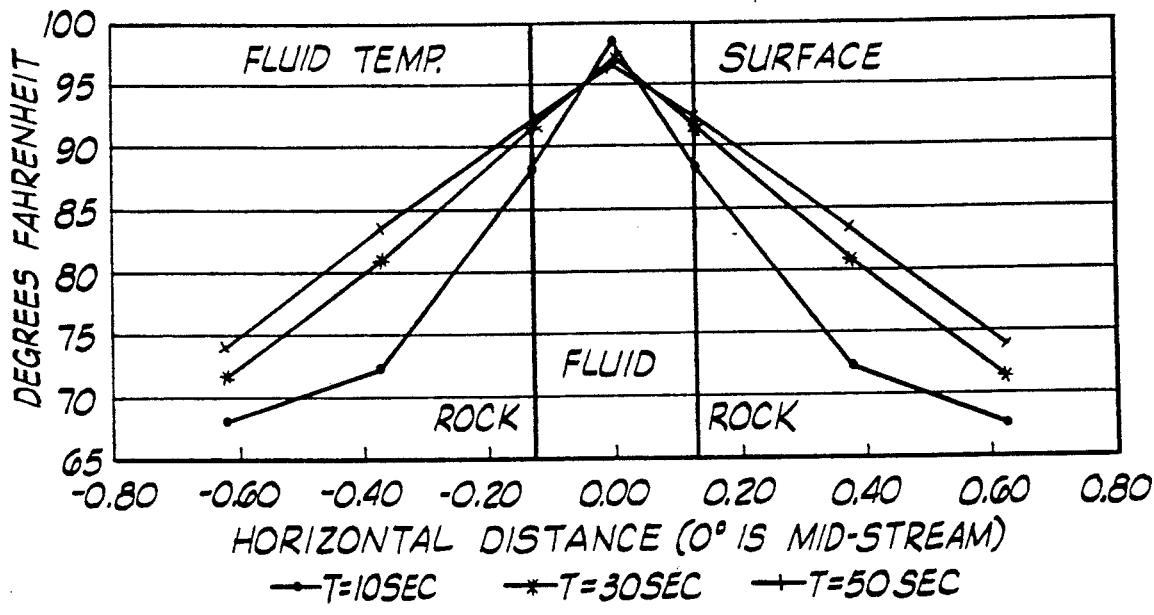
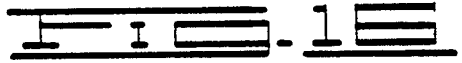
FIG. 16
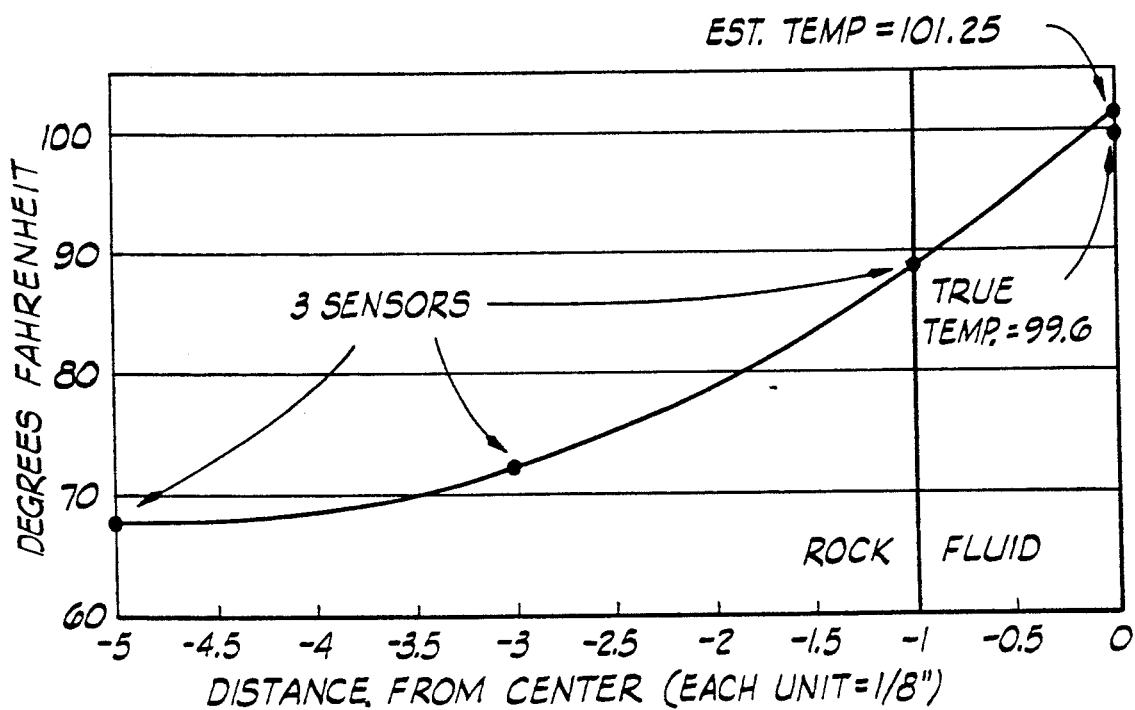
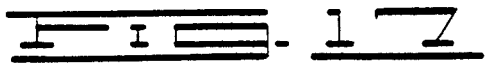
FIG. 17

5,249,864

SYSTEM FOR CHARACTERIZING TEMPERATURE OF FLUIDS

BACKGROUND

This invention relates to a system and methods for characterizing the temperature of a fluid within a testing cell, and more particularly, but not by way of limitation, a temperature sensing system and methods for estimating temperature of the fluid within a fluid testing cell for testing the behavior and characteristics of fluids under high pressures.

Fracturing fluids are used in natural gas recovery technology to increase the permeability of underground gas-laden rock. Increasing the rock permeability increases the amount of gas which can be recovered from an underground gas reservoir. The increase in permeability is obtained when fracturing fluids are pumped into the bore of the well under high pressures, thereby causing rock surrounding the well bore to fracture. These fractures may be hundreds of feet in length and, due to the great underground pressures, have a tendency to close. To reduce this tendency, a proppant such as sand is pumped along with the fluid into the bore. The proppant enters and lodges within the fracture and prevents the fracture from closing.

It has long been a goal of industry to simulate in the laboratory the shear history experienced by these fluids in the field environment. Fluids in such environments are subject to numerous and complex conditions. It is important to be able to model the rheological properties of the fluids under such conditions to be able to predict their behaviors. However, fluid models, in order to be designed and to be improved to better reflect behaviors under in-situ conditions, should be subject to simulation and experimental verification.

As an example, in order to exploit the extremely low-permeability gas reservoirs indigenous to the Tight Sands Regions of the U.S., fluid rheological and fracture propagation models need to be developed such that predictions based on these models will carry a much higher level of confidence than is currently available with existing technology.

In order to develop accurate models, the effects of many variables on the rheology of fracturing fluids with and without proppant must be thoroughly investigated. Among the variables which must be studied are temperature, fracture shear rate, fluid leak off volume, roughness of fracture walls, viscoelastic properties of gels, pressure time, proppant settling rates, proppant concentration, proppant size, proppant density and fracture dimension.

There is currently no experimental tool which can be effectively used to simulate the in-situ conditions to which fracturing fluids are subjected so these factors can be investigated.

Rheological studies on fluids flowing around objects have traditionally been performed on Hele-Shaw cells which are comprised of narrowly-separated parallel plates which allow a flow of fluid between them. At least one of the plates should be transparent to enable the viewing of the fluid flow. However, there is no system in the current rheological technology which (1) simulates the porous rock facing which exists within the well fracture, (2) allows changes in pressure, strain and shear applied to the hydraulic fluid during experimentation and (3) allows accurate measurement of important fluid parameters and properties such as velocity, pressure, and flow pattern.

BRIEF DESCRIPTION OF THE DRAWINGS

FIG. 1A is a perspective view of the front of a fluid testing cell having four module pairs.

FIG. 1B is a perspective view of the rear of a fluid testing cell having four module pairs.

FIG. 2A is a perspective view of a single rear module having an array of optical fibers.

FIG. 2B is a perspective view of a single front module having an array of optical fibers.

FIG. 3A is a perspective view of a "skeleton" of a transmitting optical fiber array present within the facing of the module in FIG. 2A.

FIG. 3B is a perspective view of a "skeleton" of a receiving optical fiber array present within the facing of the module in FIG. 2B.

FIG. 4 is a top plan cross-sectional view of a module pair having an optical fiber array.

FIG. 5A represents a side cross-sectional view of an optical fiber pressure sensing device in a non-pressurized case.

FIG. 5B represents a side cross-sectional view of the optical fiber pressure sensing device when pressure is exerted on the upper plate.

FIG. 6 is a schematic drawing of the control apparatus of the pressure sensing device exclusive of the test cell facing.

FIG. 7 is a perspective view of a test cell module showing the facing having a cavity within which the pressure sensing device is embedded.

FIG. 8 is a perspective view of a test cell module having a window through the metal back plate and rock facing.

FIG. 13 is a perspective view of a test cell module having an array of transmitting optical fibers, a pressure sensing device, and a window.

FIG. 14 is a schematic of the circular movements made by the measuring volume when flow direction is being measured.

FIG. 15 is a cross-sectional view through a rock facing showing the positions of temperature sensors.

FIG. 16 is a graph of a temperature profile derived from a set of three temperature sensors.

FIG. 17 is a graph of a second order curve fit to data from a set of three temperature sensors.

DESCRIPTION

Figure 9:
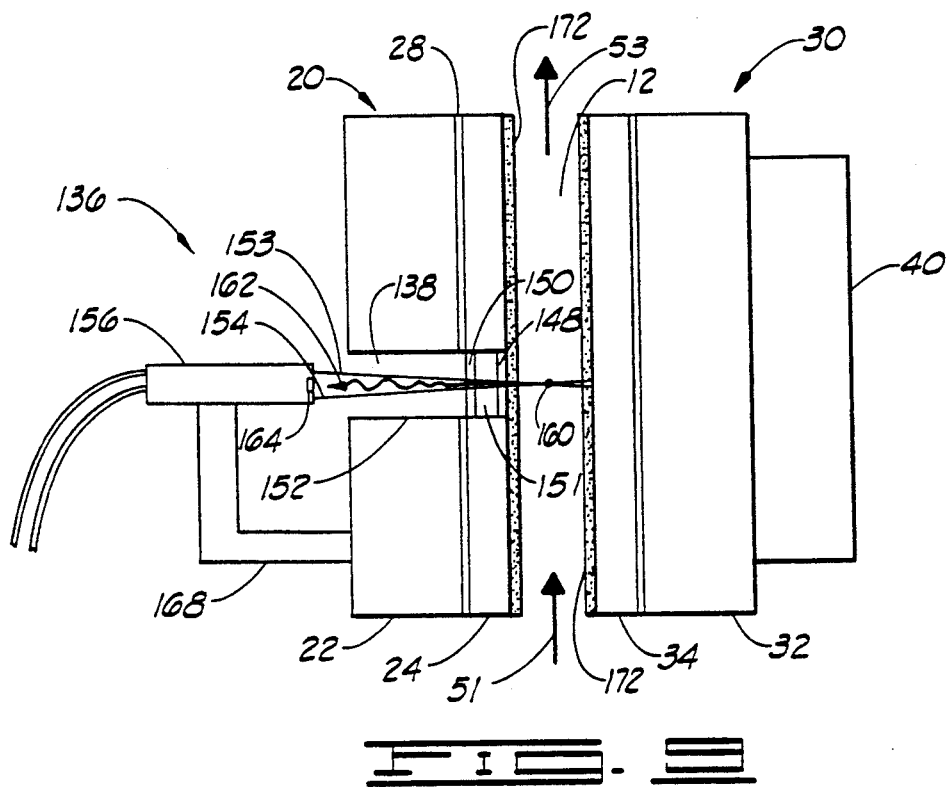
FIG. 9 is a top plan cross-sectional view of a test cell module pair showing a laser beam means aimed through the view port/window into the gap between the two rock facings of the module pair.

The object of the present invention is to provide such a system and methodology wherein such parameters and characteristics as bulk velocity, direction, filter-cake build up, pressure, temperature, and flow pattern characteristics such as proppant flow dynamics, proppant concentration, and proppant settling of a fracturing fluid can be measured and studied in a controlled situation.

The present invention comprises an apparatus and methods for characterizing fluids (which may be liquids, such as fracturing fluids, or gaseous compositions) under high pressures within a test cell or vessel. The apparatus, which in the preferred embodiment is a fracturing fluid characterization facility (FFCF), is a cell having a rock-lined lumen, or gap, into which fracturing fluid is pumped. The apparatus has means for applying pressure of varying magnitude to the fluid within the gap of the cell. The cell is rectangular and is comprised of two parallel walls spaced apart to leave the narrow lumen, or gap, into which the fluid is pumped.

A prime object of the FFCF is to characterize the physical characteristics and rheological behaviors of the fluid within the cell during the testing period. Due to the size of the gap within the cell, a gap which may have dimensions of twelve feet long by twelve feet high, it is important to be able to evaluate and measure the various fluid parameters and behaviors across the entire expanse of the cell gap, not just at a few limited sites within the gap. Therefore, measuring instruments are arrayed across the full length and height of the walls lining the cell gap.

In the present invention, the means for making these measurements are incorporated separately, or in combination, directly into the discrete modular pairs of the FFCF. The approaches to the problems of viewing the flow pattern of the fluid and of measuring pressure, velocity and temperature of the fluid have been developed and are described in detail below.

Flow Pattern Viewing

In order to be able to evaluate the status of the fluids and solids being pumped into the test cell, it is necessary to view the pattern of flow of the fluids present in the cell, thereby forming an accurate visual picture of any material, such as proppant, being transported or distributed in the fluid.

The viewing means consists of an array or matrix of fiber optic members inserted within the facings of each set of module pairs lining the flow channel or gap. Each matched fiber optic member pair includes a light transmitter and a light receiver. The fiber optic members are placed on regular coordinate grids in order to discretely illuminate the entire flow channel.

This viewing method and apparatus is superior to viewing the fluid flow directly through quartz or glass windows which offer a very limited viewing area. The fiber optic array technique allows the "viewing" of the flow over the entire area of the flow cell. The fiber optic members can be cast directly into the rock facings with the image passing easily through a conventional pipe seal behind the rock surface.

This viewing method and apparatus can also be used to help determine proppant concentration by measuring the light attenuation passing across the flow channel. In addition, the receiving fiber optic member can be multiplexed with UV radiation whereby the amount of fluorescence of the tagged fluid can be used to determine proppant concentration as well as discerning point-to-point velocity. Thus this fiber optic imaging system has numerous advantages over other viewing techniques. It offers a wide area of view, the ability to measure proppant characteristics such as concentration flow and settling, and the ability to be easily installed. In addition, it is relatively inexpensive as compared to other observation techniques such as X-ray methods, neutron imaging, borescopes, and use of quartz windows.

The preferred method used in the present invention for viewing a flow pattern of a fluid disposed between two modules of a test cell used for testing the fluid can be described as comprising the following steps. Initially is provided a first facing having a front surface, the first facing having a plurality of transmitting fiber optic members, wherein at least a portion of each transmitting fiber optic member is encased within the first facing, each transmitting fiber optic member having a transmitting end open to the front surface of the first facing. This first facing is disposed within the test cell.

Next is provided a second facing having a front surface, the second facing having a plurality of receiving fiber optic members, wherein at least a portion of each receiving fiber optic member is encased within the second facing, each receiving fiber optic member having a receiving end open to the front surface of the second facing for receiving light transmitted from a corresponding transmitting end in the first facing. This second facing is disposed within the test cell wherein the front surface of the first facing is positioned opposite the front surface of the second facing.

Light from a light source is then passed through the transmitting fiber optic members. The fluid to be studied and tested is then placed into the test cell gap and passed between the facings. Light passing through the fluid is received by the receiving fiber optic members. Light received by the receiving fiber optic members emerges from the rock facing where it may be reflected off a reflecting device such as a porroprism into a charge couple device (CDD) camera. Or, the light may be directed directly from the fiber optic bundle into the CCD camera, where the light is converted into electronic signals. This is followed by the receiving and processing of the electronic signals by a multiplexer and the conversion by a computer and terminal of the processed electronic signals into an image of the flow of the fluid. This image can be used to determine the proppant concentration, the proppant flow or the districution of settled proppant.

The fluid provided in the step of passing the fluid between the facings generally comprises a fluid having a pressure measured in a range of between zero and 1,200 pounds per square inch.

LDV Measurement

Bulk Velocity

Laser Doppler Velocimetry (LDV) measurement techniques are used to make the measurements of fluid velocity and movement in the test cell gap. The application of LDV described herein represents the first measurement of fracturing fluid point velocities in a flow vessel maintained at high temperatures (e.g., 250° F.) and pressure (e.g., 1200 psi). A fiber optic LDV technique is particularly useful in the hostile environment residing in the FFCF. A laser in the red or near infrared (provided by a semiconductor diode laser) spectrum is preferred so as to allow finite and sufficient penetration of the crosslinked fracturing fluid. LDV enables velocity measurement even at the center of the widest part of the gap. The primary measurement made is of the bulk fluid velocity, but additional signal processing can be applied to obtain the resolution of both doppler signatures: proppant, and crosslinked fluid.

Filter-Cake

Additionally, filter-cake thickness can be measured. During the flow of the fracturing fluid through the test cells, there will be some leak-off of the water contained in the fluid through the test cell rock facings. The loss of water results in the deposition of a thin layer of the gel molecules in the fluid onto the surface of the rock facing. This thin layer of gel molecules is referred to as filter-cake.

The use of LDV to measure filter-cake build up is an extension of the method of obtaining velocity of profiles of the flow. In the course of making velocity profile measurements using LDV, the measuring volume will be traversed across the flow in order to get a profile of point velocities. The measurement of filter-cake build up will take advantage of the traversal of the flow by the measuring volume. At the beginning of an experimental run it will be assumed that there is no filter-cake build up. The measuring volume will then be traversed across the flow until the point velocity reads zero indicating that the rock wall has been reached. At several later times during the run the measuring volume will again be traversed across the flow and the traverse distance to zero point velocity will be noted. The difference in the initial zero velocity distance and those distances measured at later times will give an indication of the thickness of the filter-cake and its rate of build up.

Flow Direction

In the present invention, LDV is used to measure flow direction as well. When laminar flows are studied it is generally assumed that the flow is only along one direction; however, turbulent flows cannot be assumed to be in only one direction. Since it is expected that the flow of the fracturing fluid will be turbulent, there is a need to use the LDV system to determine the direction of the flow.

A basic LDV system provides the magnitude of the velocity perpendicular to the interference fringes of the measuring volume, but does not provide the direction (from the left or from the right for example) that the flow crosses the fringes. Traditional means of measuring direction include the use of expensive electro-optic or acousto-optic devices such as Bragg cells to shift the frequency of one of the LDV beams providing a relative frequency shift to compare to the frequency shift caused by the flow. This method can be used in the present invention. However, an alternative method of direction measurement which does not rely on frequency shift has been conceived which results in significantly lower costs.

The basic principle of this alternative method is simply that the measuring volume itself will be moved against (or with) the flow resulting in a shift in the velocity data, and thus an indication of direction. If the measuring volume is moved against the flow, the magnitude of the velocity will decrease. Since only a qualitative shift in the velocity data is required to determine flow direction, an approximate technique involving the circular movement of the measuring volume has been developed. FIG. 14 illustrates this technique.

The measuring volume will be able to rotate on two separate axes. The first rotation will be about the volume's own axis and will have limits of ±90°. This rotation will allow measurement of horizontal and vertical velocity components as well as the measurement of Reynolds Stresses, which involves rotations of ±45°. The second rotation will be about an eccentric axis 1"/16 from the center of the measuring volume. This rotation will allow determination of direction for vertical and horizontal flows. As indicated in FIG. 14, as the measuring volume moves through the top of the rotation, a horizontal velocity shift will be seen depending on the direction of the flow. A similar situation holds for the vertical case where the measuring volume is rotated 90° on its own axis and it moves along the side 90° from the top of the rotation. These techniques allow the measurement of the magnitude and direction of the flow velocity in any orientation as a result of the motions of the measuring volume itself.

A dual beam system will be the type of laser anemometer used in the preferred embodiment of FFCF. The laser beam is supported by a support mechanism which is adjustable. The rock facing contains an aperture or a transparent window through which the laser beam is directed into the fluid flowing through the gap.

The following are components of the velocity measurement apparatus:

A low power semiconductor diode laser.

A beamsplitter which separates an initial beam into two beams of equal intensity.

A focusing means which causes the beams to cross and focuses individual beams.

A collecting lens which collects optical impulses and focuses them onto a photodetector.

A photodetector which converts optical impulses into electrical energy.

A signal processor which converts frequencies into readable signals.

A data processor which converts output of the signal processor into a reading of mean value, rms, amplitude probability, related to the velocities of particles in the fluid.

The optical impulses or light flux created when a particle crosses the intersection of the low focused laser beam is optically collected and focused onto a photodetector. The photodetector converts this light flux into an electrical current. Variations in this electrical current are subsequently analyzed to determine the velocity of the particle.

Photoelectron emissions in photodetectors are actually discrete events that occur at a rate proportional to the light flux incident on the photodetector. At low incident light levels, these discrete events can be analyzed by a process known as "photon correlation."

With high light fluxes, limitations on photodetector frequency response will blur out these discrete events because the signal is essentially filtered. Once this happens, additional filtering is generally added to smooth out the signal for analyzers that work on the continuous analog signal. This smoothing will remove noise which is (a) caused by the discrete nature of the original signal of interest, and (b) caused by extraneous light sources that carry no signal of interest.

The preferred method used in the present invention for LDV measurements of a fluid disposed between two facings within a test cell used for testing the fluid, generally comprises the following steps. Initially is provided a first facing having an aperture extending therethrough and having a window disposed within the aperture. This first facing is disposed within the test cell. Next, a second facing is provided and is disposed within the test cell wherein the second facing is disposed opposite the first facing. Following this a fluid can be passed between the first facing and the second facing.

Laser beam means having a first beam and a second beam are provided and both the first beam and the second beam intersect at a focal point to form a measuring volume. The laser beam means is supported by a supporting means in the vicinity of the window such that the first beam and the second beam are directable through the window toward the fluid whereby the measuring volume can be positioned within the fluid. Photodetecting means are positioned near the window for detecting optical impulses generated when particles in the fluid intersect the measuring volume. The optical impulses detected by the photodetector are converted into electrical impulses and the electrical impulses are converted into an output indicative of the velocity of the fluid.

In the step of providing the laser beam means, the laser beams means may be a semiconductor diode laser beam means. And in the step of supporting the laser beam means, the laser beam means may be adjustably supported to be moved forward and backward and rotated.

Pressure Measurement

In order to be able to make a large number of precise and cost effective fluid pressure measurements on the fluid within the test cell, pressure is measured using a device which employs fiber optic pressure transducers. In the preferred embodiment, the fiber optic pressure sensitive members have a capability of making precision differential and absolute pressure measurements in the range of 0.0 to 1200 psi with a resolution of ±0.01 psi. Such pressure transducers are cost effective and can be temperature compensated. Moreover, the fiber optic design allows the pressure readings to be easily transmitted to the outside across the pressure boundary through a small inexpensive valve feedthrough. By using a reference or compensation fiber optic member, the fiber optic transducer can also be compensated to remove any pressure distortion due to entry and exit effects.

The pressure sensing device is an orificeless surface-mounted device that will not alter the flow field in the vicinity of the device. In order to accomplish the pressure measurements, a reversibly deformable optical fiber or bundle of fibers is used. This fiber is disposed in the vicinity of the pressure that is to be measured. The distortion of the fiber by the fluid pressure will be determined by measuring the attenuation of the light energy which passes through the fiber. This attenuation is a result of the loss of the light due to the mechanical distortion of the fiber.

In the preferred embodiment, a similar optical fiber or fiber bundle serves as a reference or "control" fiber and is disposed near the pressure sensing fiber, but such that it is not subjected to the fluid pressure. This reference fiber is be used to remove from the calculation extraneous distortion due to temperature, entry, or exit effects. The fibers are passed through the rock facing into a pressure sensing zone via a narrow metal capillary conduit. Thus, the fibers enter and exit the pressure sensing zone without having been cast into the rock. Thus the fiber is relieved of any potential mechanical stresses due to the expansion and contraction of the surface rock.

The light energy that is transmitted through the fibers is characterized by its amplitude and phase, in order to gain maximum sensitivity and baseline removal for the high detailed pressure measurements. In one embodiment, only a single pressure sensing fiber is used while in another embodiment, multiple fibers can be employed for the purpose of increasing the sensitivity at high pressures.

In a preferred embodiment of the pressure sensing device, the pressure sensing fiber optic member is disposed between two plates within the rock facing. One plate, a stationary plate, is disposed rigidly in the rock facing and another plate, a movable pressure responsive plate, rests over the stationary plate. The facing sides of the stationary plate and the pressure responsive plate are corrugated. The corrugated ridges of the pressure responsive plate fit into the grooves of the stationary plate and the ridges of the stationary plate fit into the grooves of the pressure responsive plate.

When pressure is applied to the pressure responsive plate, the plate pushes the pressure sensing fiber optic member against the stationary plate, wherein the shape of the fiber optic member is deformed or distorted due to the corrugations of the two plates. As pressure is relieved, the distortion of the fiber is relieved.

In a preferred embodiment of the pressure sensing method, the method comprises the following steps. Initially is disposed a first facing within a test cell, the first facing having a cavity therein, and the cavity having a bottom surface. Next is disposed a second facing within the test cell. The next step is to provide a stationary plate having an interior surface and a deforming surface. The stationary plate is positioned within the cavity wherein the interior surface rests adjacent the bottom surface of the cavity.

Next is provided a pressure responsive plate having an exterior surface and a deforming surface. The exterior surface is substantially flush with the surface of the rock facing. The pressure responsive plate is positioned within the cavity wherein the deforming surface of the pressure responsive plate rests adjacent the deforming surface of the stationary plate. A pressure sensing fiber optic member is provided so that a pressure sensing portion is disposed within the cavity and between the deforming surface of the pressure responsive plate and the deforming surface of the stationary plate, wherein the sensing portion is reversibly deformed when pressure is exerted upon the sensing portion by the deforming surface of the pressure responsive plate.

Additionally is provided at least one reference fiber optic member having a reference portion disposed within the facing and located generally near the sensing portion of the pressure sensing fiber optic member disposed within the cavity. Light is then passed through the pressure sensing fiber optic member and through the reference fiber optic member from a light source which has been provided. A fluid is entered into the gap and is caused to be passed between the first facing and the second facing.

A first light signal is detected from the pressure sensing fiber optic member and a second light signal is detected from the reference fiber optic member. Using a comparing means, which may be computer software, the first light signal is compared to the second light signal and a pressure reading determined therefrom is outputted.

Temperature Sensing/Estimation

There is currently a need for temperature data-acquisition in fracturing fluid models which measures or estimates the temperature of the fluid. The measurement technique should be noninvasive (i.e., sensors are not put directly into the flow of the fluid) so that the natural characteristics of the flow will not be disturbed.

Therefore, the sensors must be imbedded into the rock facing. However, a single sensor imbedded in the rock facings is not sufficient to accurately represent the temperature of the fluid. Even a single surface-mounted sensor on the boundary of the rock/fluid interface would be greatly affected by the ambient temperature of the rock facing. For example, in the event of a thermal transient in the fluid, the single surface mounted sensor would not be capable of following this instantaneous rise or fall in fluid temperature.

The solution to this problem is one which incorporates measuring not only the temperature at the rock/fluid interface, but the temperature at different depths of the rock facing. From these measurements, a temperature gradient can be measured in the rock facing. Using this gradient, the bulk temperature of the fluid can be obtained by projecting the gradient curve beyond the rock/fluid interface to estimate a temperature.

Experimentation has shown that three data points are sufficient to characterize the temperature gradient in the rock facing. Taking data points at three different depths of the rock provides sufficient information to perform a first or second order curve fit since the spacing of the sensors is known. Once the coefficients of the equation are determined, the curve can be projected into the flow of the fluid. From this curve, a fluid temperature can be estimated.

Actual data showing the results of a thermal transient (hot water at t=0 sec) flowing in a one-quarter inch gap can be seen in FIG. 16. The sensors in the rock facing were spaced one-quarter inch apart beginning with the one on the rock/fluid interface. It is obvious from this data that an accurate measurement of the fluid temperature cannot be made from a single surface mounted sensor alone.

FIG. 17 shows an example of the curve fitting/projecting technique. From the three sensors, a second order curve can be fitted to the data using the least-squares method of polynomial regression. The curve is then projected beyond the surface of the facing into the flow to provide an estimated temperature of the fluid. This is actual experimental data proving that the technique is a valid one. The equation is of the form:

$$T_{est} = C_0 + (C_1)(DISTANCE) + (C_2)(DISTANCE)^2$$

In this equation $C_0$, $C_1$ and $C_2$ are the coefficients which were calculated using the least squares polynomial regression. DISTANCE is horizontal distance between sensors in the rock facing. $T_{est}$ is the estimated temperature of the fluid.

Each measurement is made with a temperature probe or sensor which in the preferred embodiment comprises a thermistor. This is an electrical component having a resistance dependent upon the temperature of its immediate environment. When accompanied by a signal conditioner, any change in resistance is converted into a change in dc voltage. For this application, the signal conditioner is calibrated to provide a linear voltage which is 0 V at 50 degrees Fahrenheit and 5 V at 250 degrees Fahrenheit.

This voltage is then changed to a digital value by a 486-based analog-to-digital (a/d) converter. The digital data is read by a computer program which performs the curve fit and estimation procedure described above. With the speed of the 486 data-acquisition system combined with its rapid computing ability, the entire procedure is virtually operating in "real-time". The final result is a single temperature estimation in degrees Fahrenheit. This information is then logged on disk and/or passed to another program for graphical presentation.

The accuracy of this measurement technique is a function of time. As a thermal transient occurs, there is a different rise time for each sensor in the rock. Therefore the temperature profile will be quite drastic (steep) for a short period of time followed by a slow "flattening out" procedure. During this period of time, the projection of the curve will sometimes exhibit a small overshoot of the actual temperature, and sometimes it will undershoot the true temperature of the fluid. However, in all cases, the projection technique provides much better accuracy than just having the single surface mounted sensor on the rock/fluid interface.

Materials and Sources

The following are examples of commercially-available components which can be used in the embodiments of the invention described herein.

| Fiber Optic Pressure Transducer | | | |
|---|---|---|---|
| Components | Manufacturer | Part # | Description |
| LED'S | Honeywell | HFE 4854-014 | 850 nm, ST connectorized |
| 3 dB Coupler | Fiberlink | 946-11106-1200 | 850, 1 × 2, ST connectorized |
| Photodetectors | Honeywell | HFD 3854-002 | PIN photodiode, ST connectorized |
| Fiber | Fiberguide Industries | SFS100/140A | 100/140 multimode Al coated silica fiber |
| Connectors | Fiberlink | 953-102-5003 | ST type, 231 μm |
| Adapters | Fiberlink | 953-120-5000 | ST type |

| Fiber Optic Viewing Apparatus | | | |
|---|---|---|---|
| Component | Manufacturer | Part # | Description |
| Fiber (Source & Sink) | Moritex | PGR-FB1000 | Polymer fibers (1000 microns dia.) |
| Cameras | Sony | XC-77 | CCD, b/w, 0.5 Lux |
| Prisms | Edmund Scientific | A32333 | 15 mm × 21 mm × 15 mm |
| Frame grabber | Data Translation | DT2851 | |
| Computer | Gateway 2000 | 486/33C | 486 DX, 33 MHz |
| Video Multiplexer Chip | Harris | HI1-506A | IC's used to multiplex several CCD outputs to one Frame grabber |
| RGB to NTSC Converter | | Laird 1032 encoder | Used to converter output of frame grabber |
| VCR | JVC | HRS4700U | Super VHS recoder |
| Monitor | | | |

| Laser Doppler Velocimetry | | |
|---|---|---|
| Components | Manufacturer | Model # |
| Laser Probe | TSI Incorporated | 6860 |
| Laser Probe Power Supply | TSI Incorporated | 6810 |
| Intelligent Flow Analyzer | TSI Incorporated | IFA550 |
| Flow INformation Display (FIND) Software | TSI Incorporated | |
| IFA 550 Realtime Analysis Display Software | TSI Incorporated | |

Description of the Test Cell Apparatus

As explained above, the present invention comprises an apparatus as well as methods for characterizing fracturing fluids under high pressures. Turning now to FIGS. 1A and 1B, the apparatus, or fluid test cell is a cell lo which has a lumen, or gap 12, which is lined with rock facing, and into which fracturing fluid (not shown) is pumped. The cell 10 has means (discussed in more detail below) for applying pressure to the fluid within the gap 12 of the cell 10 at variable magnitudes and at varying locations within the cell 10. The cell 10 is substantially rectangular in dimension and is comprised of a first wall 14 parallel to a second wall 16. The first wall 14 and the second wall 16 are adjustably spaced apart to leave the gap 12 into which the fluid is pumped. The cell gap 12 is enclosed by a covering means comprising an upper side cover (not shown) on the upper side and a base plate 18 on the lower side. Each wall 14 and 16 is comprised of a plurality of discrete modules. Wall 14 is comprised of a plurality of stationary modules 20.

Each stationary module 20 is stationary during the operation of the test cell 10 but each is removable and replaceable during interludes between testing operations of the cell 10. As shown in FIG. 2A each module 20 is comprised of a metal back plate 22 having a height 23a, a width 23b and a depth 23c. A rock facing 24 having a front surface 24a and a rear surface 24b is attached to the metal backing 22. The facing 24 has a height 25a, a width 25b and a depth 25c.

The facing 24 is a man-made rock surface which in one embodiment is comprised of a mixture of Class H Portland cement and a silica flour comprising pure quartz particles having a 200-325 mesh size. Both products are commercially available. Water is added to the cement for hydration. Approximately 70% of the set cement consists of calcium-silicate hydrate with minor amounts of calcium aluminum hydrate and trisulfoaluminate hydrate (ettringite). Monosulfate and portlandite are the major reaction products. The silica flour is used as an additive to regulate permeability and to prevent strength regression at high temperatures (>230 degrees F.). In other embodiments, the facing 24 may be comprised of other types of cement or compositions which provide a similar porous rock-like surface.

The facing 24 is attached to the metal backing 22 with an attaching means 26 which in the preferred embodiment are bolts. A screen 28 may be sandwiched in between the surface 24b of the facing 24 and the metal backing 22 to provide a means for bleeding off fluid which may diffuse through the porous rock facing 24.

Wall 16 is comprised of a plurality of movable modules 30. In the preferred embodiment, having twelve modules 20 and twelve modules 30, each stationary module 20 of wall 14 is located opposite to a corresponding movable module 30 of wall 16 and the number of modules 20 is equal to the number of modules 30. In an alternative embodiment the number of modules 20 may not be equal in number to the number of modules 30 and may not be located correspondingly opposite one another.

Each movable module 30 is movable during the operation of the test cell 10 and each is removable and replaceable during interludes between testing operations of the cell 10. As shown in FIG. 2B each module 30 is comprised of a metal backing 32 having a height 33a, a width 33b and a depth 33c. A rock facing 34 having a front surface 34a and a rear surface 34b is attached to the metal backing 32. The facing 34 has a height 35a, a width 35b and a depth 35c. The facing 34 is a simulated rock surface which in the preferred embodiment has a composition identical to or similar to the composition of the facing 24 described above.

The facing 34 is attached to the metal backing 32 with an attaching means 36 which in the preferred embodiment are bolts. A screen 38 may be sandwiched in between the surface 34b of the facing 34 and the metal backing 32 to provide a means for bleeding off fluid which may diffuse through the porous rock facing 34.

Each of the modules 30 of the second wall 16 is attached to a hydraulic actuator 40 as indicated in FIGS. 1A and 2B and is movable a variable distance in relation to the corresponding stationary module 20. Each movable module 30 is discrete and can be moved independently of each other movable module 30. The test cell 10 of the preferred embodiment is thereby comprised of a plurality of module pairs 20 and 30, the stationary module 20 in the pair positioned opposite the movable module 30. The actuators 40 are generally supported by a support or buttressing means 42 which serve to buttress the actuators 40 when the actuators 40 are exerting pressure on the modules 30. A single buttressing means 42 is represented in FIG. 1A. The stationary modules 20 are also supported by a support or buttressing means, (not shown). Each hydraulic actuator 40 moves a module 30 connected thereto in a direction 41 (FIG. 2B) generally toward a corresponding module 20 and in a direction 43 (FIG. 2B) generally away from the module 20.

The front surface 24a of the facing 24 faces the front surface 34a of the facing 34 across the gap 12 as indicated in FIGS. 1A and 1B. The front surface 24a and front surface 34a are thereby exposed to the fluid (not shown) which is pumped into the gap 12. Because the rock of the rock facings 24 and 34 is porous, fluid under pressure may seep through the facings 24 and 34. Fluid which migrates through the facings 24 and 34 this way is collected within screens 28 and 38 sandwiched within the modules 20 and 30, respectively, and is bled away out of the cell 10.

Fluid is supplied under pressure in direction 51 (FIG. 1A) to the cell gap 12 of the cell 10 via a pipe 50 which feeds an input manifold 52 (FIG. 1A) which also serves as a first side cover of the first side of the gap 12. Fluid can be drained from the cell gap 12 in a direction 53 via an output manifold 56 (FIG. 1A), which also serves as a second side cover of the second side of the gap 12, and through a pipe 58 (FIGS. 1A and 1B). While the fluid is within the cell gap 12, pressure can be exerted upon the fluid by causing at least one actuator 40 to actuate a movable plate module 30 against the fluid in the gap 12, thereby increasing the pressure of the fluid within the gap 12.

The test cell 10 comprises at least one measuring means for measuring a parameter of the fluid. In the case in which the parameter is related to the flow pattern of the fluid, the measuring means is a viewing apparatus.

The metal backings 22 and 32 and rock facings 24 and 34 of the modules 20 and 30 are opaque and thereby prevent direct viewing of the flow patterns of the fluid within the cell gap 12. Therefore, in order to be able to view of the fluid flow pattern, a viewing system comprised of a plurality of transmitting and receiving optical fibers is incorporated into the facings 24 and 34 of the test cell 10.

The parameter may be related to the pressure or movement of the fluid. In this case, the measuring means is a pressure sensing apparatus or a movement measuring apparatus, respectively. If the parameter is related to temperature of the fluid, the measuring means is a temperature estimating apparatus.

Viewing Apparatus

Turning now to FIGS. 2A–4, the viewing apparatus (fiber optic imaging device) 59 for producing an image of the flow pattern of the fluid disposed within the gap 12 of a test cell 10 is described. The test cell 10 comprises at least a first facing 24 and at least a second facing 34. When arranged within the test cell 10, the first facing 24 is disposed opposite the second facing 34 as indicated in cross-section in FIG. 4.

Disposed within the first facing 24 of the apparatus 59 is a plurality or array 60 (FIG. 3A) of transmitting fiber optic members 62 entering the facing 24 through a cable 61. The array 60 is distributed as a matrix of transmitting fiber optic members 62. Each transmitting fiber optic member 62 has a transmitting end 64. The array 60 is embedded or encased into the facing 24. Each transmitting end 64 is exposed at the front surface 24a of the facing 24 as indicated in FIG. 2A. The transmitting ends 64 are thereby exposed to the gap 12 of the test cell 10 as shown in FIGS. 2A and 4.

Disposed within the second facing 34 of the apparatus 59 is a plurality or array 70 (FIG. 3B) of receiving fiber optic members 72 distributed as a matrix of receiving fiber optic members 72, and appearing substantially as a mirror image of the array 60 of FIG. 3A. Each receiving fiber optic member 72 has a transmitting end 74. The array 70 is embedded or encased into the facing 34 in the same manner as the array 60 is embedded into facing 24. Each receiving end 74 is exposed at the front surface 34a of the facing 34 (FIG. 4). The receiving ends 74 are thereby exposed to the gap 12 of the test cell 10. The receiving fiber optic members 72 exit the facing 34 as a plurality or bundle 71 (FIG. 4) which is attached to a light conversion unit 76 (FIG. 4).

The purpose of each receiving end 74 of each receiving fiber optic member 72 is to receive light impulses 66 which are transmitted from a transmitting end 64 of a transmitting fiber optic member 62 of the first facing 24 across the gap 12 through the fluid within the gap 12 (FIG. 4). Toward this end, each receiving end 74 of the second facing 34 is disposed opposite to and in corresponding alignment with the transmitting end 64 of one of the transmitting fiber optic members 62.

The viewing apparatus 59, further comprises such as a light source 73 such as a light bulb or light emitting diode which is used to cause light to be transmitted through the transmitting fiber optic members 62 and therein through the transmitting ends 64 of the first facing 24. Light impulses 66 which pass through the fluid (not shown) are received by the receiving ends 74 of the receiving fiber optic members of the second facing 34 and carried from the facing 34 through the bundle 71 into the light conversion unit 76.

The light conversion unit 76 converts the light impulses into electronic signals which are received and processed by a signal receiver and processor 77 which processes the signals and converts them into an image of the fluid flow displayed on the image display unit 79. The image may be used to measure the proppant concentration of the fluids, or to assess dynamic flow or settling of the proppant within the fluid.

Pressure Sensing Apparatus

Turning now to FIGS. 5A–6, the pressure sensing apparatus (fiber optic pressure sensing device) 80 for measuring a pressure of fluid disposed within the gap 12 between at least two facings of a test cell 10 is discussed. The pressure sensing apparatus 80 comprised first of a movable, pressure responsive plate 82. The pressure responsive plate 82 has a first surface 84 which is substantially flat and a deforming surface 86 which in the preferred embodiment is corrugated with ridges 88 and grooves 89 between the ridges 88. The pressure sensing apparatus is further comprised of a stationary plate 92 having a first surface 94 which is substantially flat and a deforming surface 96 for engaging which in the preferred embodiment is corrugated with ridges 98 and grooves 99 between the ridges 98.

The term "corrugated" is meant here as a surface having at least one ridge or at least one groove. For example in another embodiment, the pressure responsive plate 82 may have a single ridge 88 on the surface 86 which can engagingly engage with a single groove 99 on the surface 96 of the stationary plate 92.

The pressure responsive plate 82 rests generally over the stationary plate 92 such that the corrugated ridges 88 of the pressure responsive plate 82 rest generally opposed to the grooves 99 of the stationary plate 92. Similarly, the ridges 98 of the stationary plate 92 rest generally opposed to the grooves 89 of the pressure responsive plate 82. A gap 90 (FIG. 5A) occurs generally between the second surface 86 of plate 82 and the second surface 96 of plate 92. The two plates 82 and 92 are disposed within a cavity 81 (shown in FIG. 7) in the rock facing 24 of the module 20. Although the pressure sensing apparatus 80 is discussed herein as being disposed in the first rock facing 24, it will be understood by one of ordinary skill in the art that a pressure sensing apparatus could also be disposed in the second rock facing 34, or indeed in both rock facings 24 and 34 of the same module pair.

As shown in FIG. 7, the first surface 94 of the stationary plate 92 rests against and may or may not be firmly attached to the bottom 81c of the cavity 81. The pressure responsive plate 82 rests over the stationary plate 92 within the cavity 81. The cavity 81 has a depth 81a and a diameter 81b. The two plates 82 and 92, when disposed within the cavity 81 rest generally entirely within the cavity 81 such that the surface 84 of the pressure responsive plate 82 is substantially flush with the surface 24a of the facing 24 (FIG. 5A) and the pressure responsive plate 82 is adjacent the fluid within the gap 12 of the test cell 10.

At least one reversibly distortable pressure sensing fiber optic member 100 (FIGS. 5B and 6) is at least partially disposed within the gap 90 between deforming surface 86 of the pressure responsive plate 82 and deforming surface 96 of the stationary plate 92. By reversibly distortable is meant an optic fiber having elastic properties such that it is not permanently deformed by pressures exerted upon it. The pressure sensing member 100 is oriented within the gap 90 such that the pressure sensing member 100 is not parallel to the longitudinal axes of the ridges 88 and 98 and grooves 89 and 99 of plates 82 and 92.

The plates 82 and 92 and the pressure sensing fiber optic member 100 disposed between them may be encased within a thermoplastic material (not shown) or alternatively a thermoplastic cap (not shown) may rest over surface 84 of plate 82, or place 82 will be made of a corrosion resistant material, e.g., stainless steel, to protect the pressure responsive plate 82 from the corrosive effects of the fluid within the gap 12.

The pressure sensing fiber 100 passes through a first port 102 via an input conduit 104 within the facing 24 and enters the cavity 81 and passes between the plates 82 and 92. The fiber 100 passes out of the cavity 81 at a second port 106 and into an output conduit 108 in the facing 24 whereby the fiber 100 then passes out of the facing 24.

As pressure from the fluid within the gap 12 presses against the pressure responsive plate 82 in a direction 101, the plate 82 is pushed against the pressure sensing fiber optic member 100 thereby deforming it between the deforming surface 86 of plate 82 and the deforming surface 96 of plate 92. This deformation causes an attenuation of the light energy passing through the fiber optic member 100. When the pressure responsive plate 82 depresses against the pressure sensing fiber optic member 100, the surface 84 of the plate 82 may be depressed a variable distance 103 below the surface 24a of the facing 24.

Optionally, at least one reference or compensation fiber optic member 110 is disposed near the pressure sensing cavity 81 and thereby in the vicinity of the pressure sensing fiber optic member 100 for the purpose of detecting "noise" or artifacts which may exist within the system and which need to be factored out, or compensated for, to derive an accurate pressure reading. The reference fiber 110 is disposed within a conduit 112 which is embedded within the rock facing 24.

Both the pressure sensing fiber 100 and the reference fiber 110 are supplied with light from the light source 118. Thus, as indicated in FIG. 6, the fiber 100 passes between the plates 82 and 92 in direction 120 and exits the plates 82 and 92 in direction 122, where its end is coupled to a pressure receiver 124. The pressure receiver 124 serves as a first light detecting means for detecting a first light signal from the pressure sensing fiber 100. The attenuation of the light passing through the pressure sensing fiber 100 is detected by the pressure receiver 124.

Upon its exit from the facing 24, the end of fiber 110 is coupled with a compensation receiver 126 (FIG. 6) which serves as a second light detecting means for a second light signal obtained from the reference fiber 110. The first signals from the pressure receiver 124 and the second signals from the compensation receiver 126 are evaluated with a comparator or comparing means 128 Which compares the first light signal to the second light signal and thereby accounts for "background" artifacts detected by the reference fiber 110 and a pressure reading 130 is outputted.

Movement Measuring Apparatus

Figure 10:
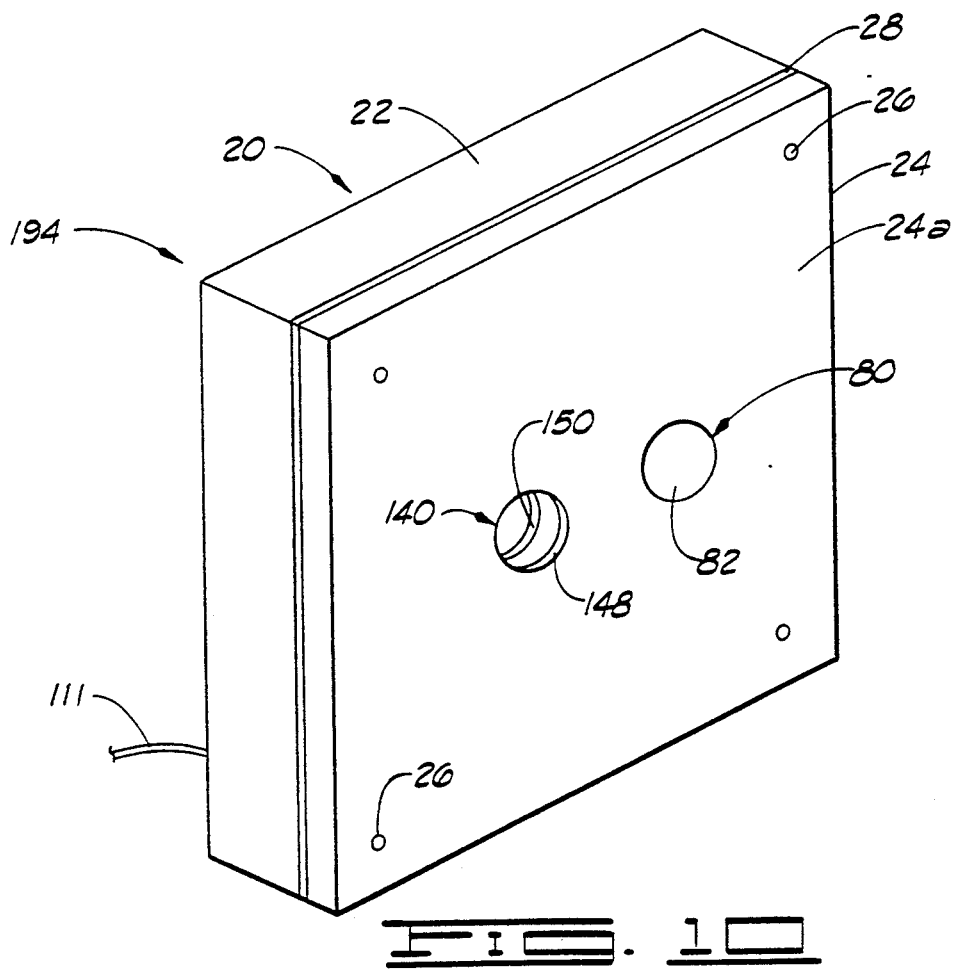
FIG. 10 is a perspective view of a test cell module having a pressure sensing device and having a window.

Turning now to FIGS. 9, 10 and 14, the movement measuring apparatus (laser Doppler velocimetry device) 136 is shown in FIG. 9 for measuring the movement of fluid disposed within the gap 12 between at least two facings of a test cell 10 is comprised of a facing such as the facing 24. The facing 24 further comprises an aperture 138 having a window 140 (FIG. 10) disposed therein and extending therethrough. In one embodiment the window 140 is composed of a first piece 148 (FIGS. 9 and 10) flush with the outer surface 24a of the facing 24 and a second piece 150 (FIGS. 9 and 10) which is flush with the inner surface 24b of the facing 24 wherein a portion 151 of the aperture 13B remains void between the first piece 148 and the second piece 150. In an alternative embodiment the window 140 is solid and extends at least partially from surface 24a to surface 24b.

In a preferred embodiment, the facing 24 having the window 140 is attached to a metal backing 22 having a bore 152 (FIG. 9) extending therethrough and aligned with the aperture 138 and thereby with the window 140 of the facing 24 such that the window 140 is visible through the metal backing 22.

The apparatus 136 further comprises a first laser beam 153 and a second laser beam 154 provided by a laser probe 156 which is supplied with laser light by a laser diode, a beamsplitter (not shown), and an energy source (not shown). In the preferred embodiment the laser is a semiconductor diode laser. The first beam 153 and the second beam 154 are focused to intersect wherein is formed a measuring volume 160 (FIG. 9).

Optical impulses 162 (FIG. 9) are generated by particles within the fluid which intersect with the measuring volume 160. Optical impulses 162 are detected by a photodetecting means such as the photodetector 164 (FIG. 9) which in the preferred embodiment is located within the laser probe 156. The apparatus further comprises optical impulse conversion means (not shown) for converting the detected optical impulses 162 into electrical impulses. An electrical impulse conversion means (not shown) then provides an output indicative of the movement of the fluid.

The apparatus 136 further comprises support means 168 (FIG. 9) attached to the metal backing 22 for supporting the laser probe 156 in the vicinity of the window 140 such that the first beam 153 and the second beam 154 can be directed through the window 140 toward fluid within the gap 12 thereby locating the measuring volume 160 within the fluid. In the preferred embodiment, the support means 168 is adjustable backward and forward, side-to-side, or radially, such that the position of the probe 156 can be adjusted to alter the relative position of the measuring volume 160 within the gap 12.

The movement measuring apparatus 136 functions to measure the fluid parameters of bulk velocity, filter-cake build up and flow direction. Point measurements of bulk velocity are made where the measuring volume 160 intersects the fluid within the gap 12. Filter-cake build up 172 is determined by altering the position of the laser probe support means 168 in a forward backward direction relative to the front surface 34a of the rock facing 34 opposite the laser probe 156. The measuring volume 160 is traversed across the flow of the fluid to determine the point of zero velocity.

Flow direction can be determined by moving the measuring volume 160 in relation to the flow of the fluid within the gap 12 as illustrated in FIG. 14. The measuring volume 160 is first rotated in direction 174 up to 90°. about its own axis 175. The measuring volume 160 is then rotated in a second direction 176 about an eccentric axis 177. These techniques allow the measurement of the magnitude of the direction of fluid flow in any orientation.

Temperature/Estimating System

Turning now to FIG. 15, the temperature estimating system is comprised of a temperature sensing apparatus 180 which comprises a first temperature sensor 182, a second temperature sensor 184, and a third temperature sensor 186. In the embodiment represented herein, the temperature sensors 182, 184, and 186, are thermistors available commercially from a number of sources.

The first temperature sensor 182 is embedded in the rock facing 24 in a position in which the sensor 182 is substantially flush with the front surface 24a facing 24 and does not extend into the overall direction of the flow of the fluid within the gap 12, the overall direction of the flow of fluid being shown in FIGS. 4 and 15 with the numerals 51 and 53.

The second temperature sensor 184 is embedded in the same rock facing 24 in a position which is in horizontal alignment with a first distance 188 directly behind the first temperature sensor 182.

The third temperature sensor 186 is embedded in the same rock facing 24 as the first temperature sensor 182 and the second temperature sensor 184. The third temperature sensor 186 is positioned in horizontal alignment a second distance 188 directly behind the second temperature sensor 184, the first and second distances being equal as shown in FIG. 17. The first temperature sensor 182, the second temperature sensor 184 and the third temperature sensor 186 are thereby located in a substantially linear alignment in the facing 24 and in a perpendicular direction with respect to the overall direction of the flow of fluid. In the embodiment describe 188 is approximately one-quarter inch.

FIG. 15 indicates the presence of four three-sensor temperature sensing apparatuses 180. However, it will be understood by on skilled in the art that substantially fewer or more temperature sensing apparatuses 180 may be found in a given facing 24. Only one temperature sensing apparatus 180 is required to provide data for an estimate of the temperature of the fluid.

The temperature sensors 182, 184, and 186, are connected by leads 190a, 190b, and 190c, respectively, to a signal conditioner (not shown) which detects a resistance signal from the sensors 182, 184, and 186, and converts the signals into data. The data are then used as input to a computer (not shown) for calculating a regression curve, from which an estimate of the fluid temperature is calculated and outputted.

Combinations of Apparatus

Figure 11:
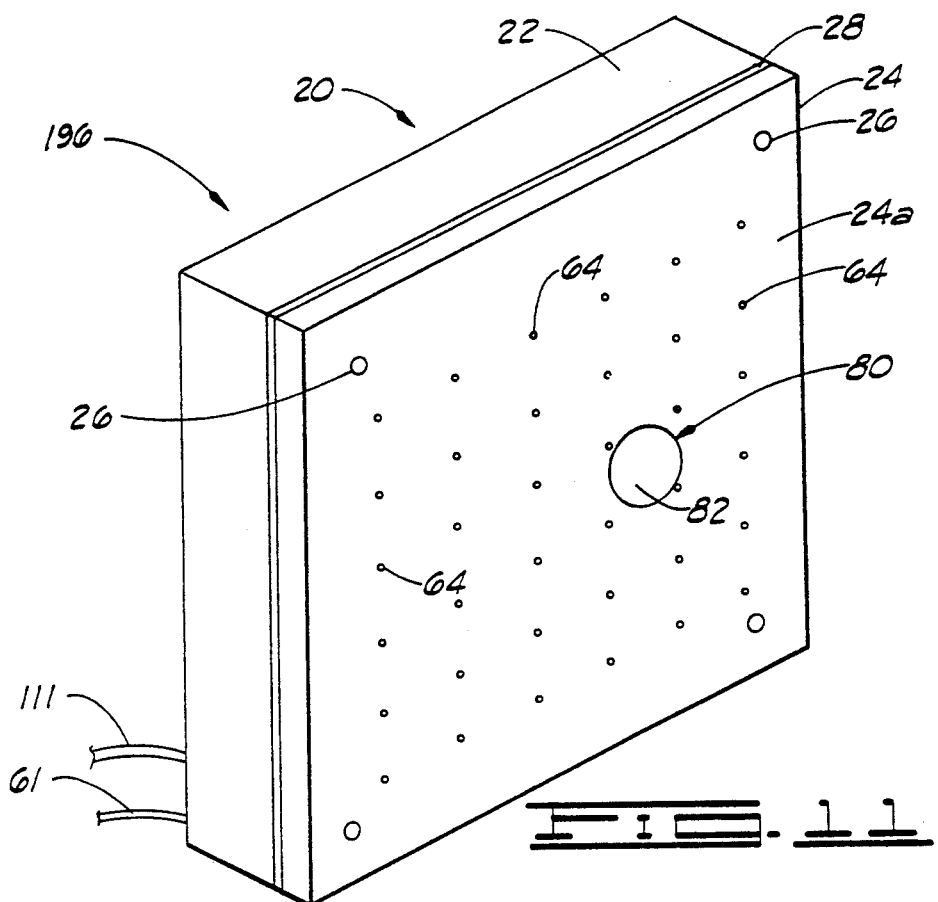
FIG. 11 is a perspective view of a test cell module having an array of transmitting optical fibers and a pressure sensing device.
Figure 12:
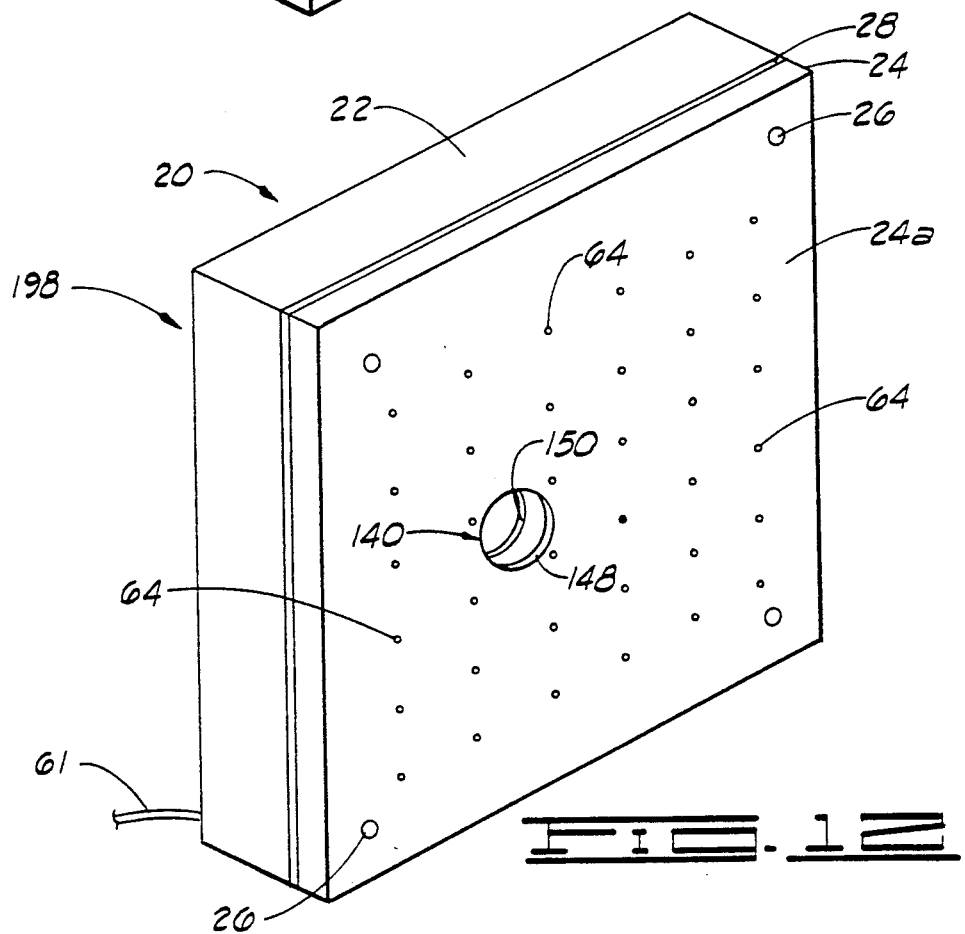
FIG. 12 is a perspective view of a test cell module having an array of transmitting optical fibers and a window.

The present invention contemplates combinations of the imaging apparatus 59, the pressure measuring apparatus 80 and the movement measuring apparatus 136 and the temperature sensing apparatus 180. FIG. 10 illustrates a movement/pressure system 194 comprised in part of a module 20 having a facing 24 which has combination of the movement measuring apparatus 136 (represented by the window 140) and the pressure sensing apparatus 80. FIG. 11 illustrates an viewing/pressure system 196 comprised in part of a module 20 having a facing 24 which represents a combination of the viewing system 59 and the pressure sensing apparatus 80. FIG. 12 illustrates an viewing/movement system 196 comprised in part of a module 20 having a facing 24 which represents a combination of the viewing system 59 and the movement measuring apparatus 136 as represented by the presence of the window 140. FIG. 13 illustrates an viewing/movement/pressure system 200 comprised in part of a module 20 which has a facing 24 which represents a combination of the viewing system 59, the movement measuring apparatus 136, and the pressure sensing apparatus 80.

Figure 18:
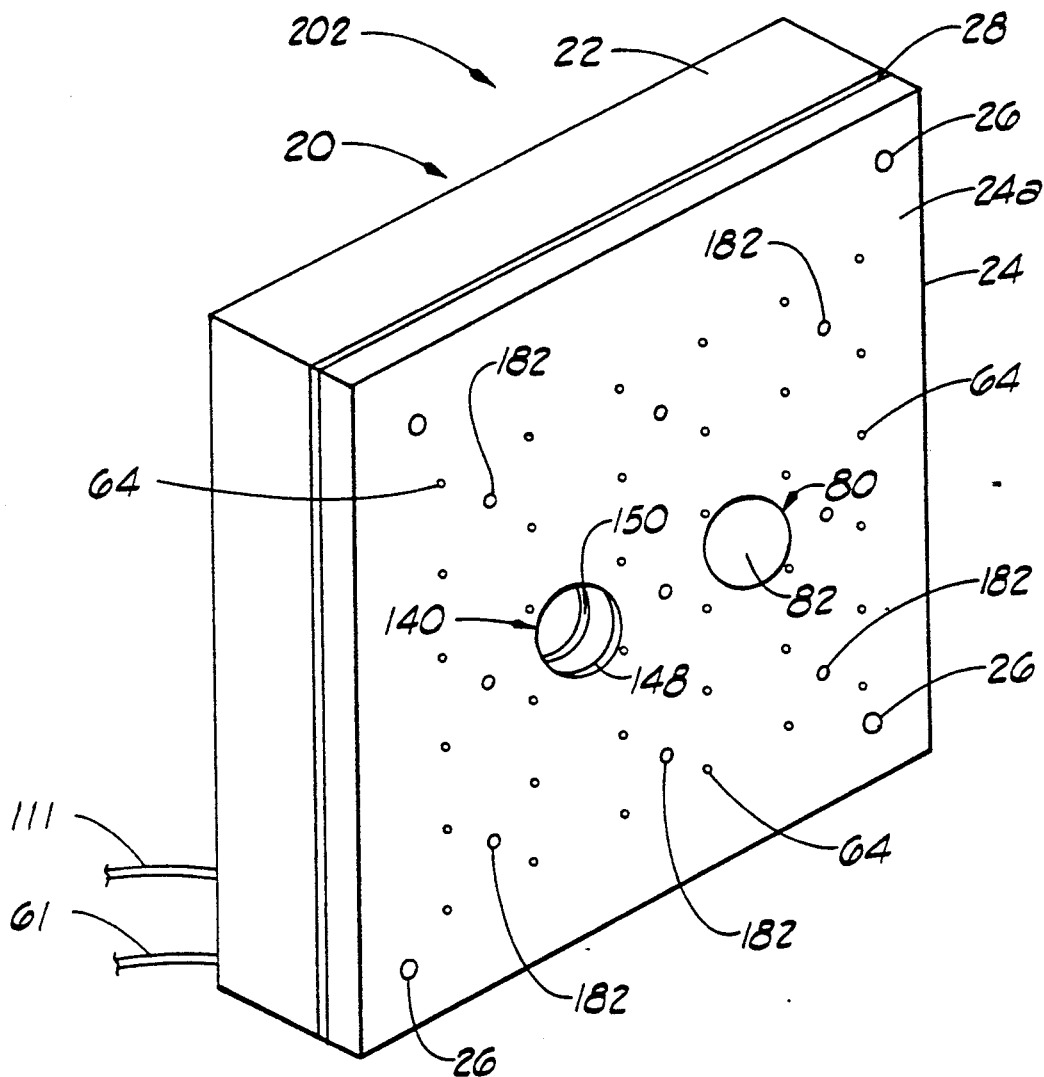
FIG. 18 is a perspective view of a test cell module having an array of transmitting optical fibers, a pressure sensing device, a window and an array of temperature sensors.

FIG. 18 illustrates a viewing/movement/pressure/temperature system 202 comprised in part of a module 20 which has a facing which represents a combination of the viewing system 59, the movement measuring apparatus 136, the pressure sensing apparatus 80, and the temperature sensing apparatus 180.

Other combinations of the various sensing devices which are not illustrated herein by drawings can be easily envisioned by one of ordinary skill in the art. It will also be appreciated that the sensing devices described herein may be arranged in various combinations in regard to their locations within the first facing 24, the second facing 34, or even within both the first facing 24 and the second facing 34.

Changes may be made in the embodiments of the invention described herein or in parts of the elements of the embodiments described herein of in the steps or in the sequence of steps of the methods described herein without departing from the spirit and scope of the invention as defined in the following claims.

What is claimed is:

1. An apparatus for estimating a temperature of a fluid having a flow in an overall direction, the apparatus comprising:

a facing having a front surface and a rear surface, the front surface of the facing disposable adjacent the fluid;

a first temperature sensor embedded in the facing in a first sensor position wherein the first temperature sensor is substantially flush with the front surface of the facing;

a second temperature sensor embedded in the facing in a second sensor position which is aligned horizontally a first distance directly behind the first sensor position;

a third temperature sensor embedded in the facing in a third sensor position which is aligned horizontally a second distance directly behind the second sensor position, said second distance being equal to said first distance, and wherein the first temperature sensor, the second temperature sensor, and the third temperature sensor are located in a substantially linear horizontal alignment within the facing and in a perpendicular direction with respect to the overall direction of the flow of fluid;

signal detecting/converting means connected to each temperature sensor for detecting signals from the temperature sensors and converting the signals into data; and temperature outputting means for receiving the data and for outputting an estimated fluid temperature reading calculated from the data.

2. The apparatus of claim 1 wherein the temperature sensors are thermistors.

3. The apparatus of claim 1 wherein the facing is supportable within a test cell.

4. The apparatus of claim 1 further comprising a second facing disposed opposite the first facing wherein a gap is formed therebetween for containing the fluid.

5. The apparatus of claim 1 wherein the facing is further comprised of simulated rock.

6. A method for estimating a temperature of a fluid having a flow in an overall direction, the method comprising the steps of:
   providing a test cell the test cell having disposed therein:
      a facing having a front surface and a rear surface,
      a first temperature sensor positioned in the facing in a first sensor position wherein the first temperature sensor is substantially flush with the front surface of the facing,
      a second temperature sensor positioned in the facing in a second sensor position which is aligned horizontally a first distance directly behind the first sensor position, and
      a third temperature sensor positioned in the facing in a third sensor position which is aligned horizontally a second distance directly behind the second sensor position, said second distance being equal to said first distance, and wherein the first temperature sensor, the second temperature sensor, and the third temperature sensor are located in a substantially linear horizontal alignment within the facing and in a perpendicular direction with respect to the overall direction of the flow of fluid;
   passing the fluid by the front surface of the facing;
   detecting a signal from each temperature sensor and converting the signals into data; and
   receiving the data and calculating an estimated fluid temperature reading therefrom.

7. The method of claim 6 further comprising the steps of providing a second facing and disposing the second facing opposite the first mentioned facing wherein a gap is formed therebetween for containing the fluid.

8. The method of claim 6 wherein in the step of calculating an estimated fluid temperature, a regression curve is fit to the data and the estimated fluid temperature is obtained by projection from the curve.

* * * * *

UNITED STATES PATENT AND TRADEMARK OFFICE
CERTIFICATE OF CORRECTION

PATENT NO. : 5,249,864

DATED : Oct. 5, 1993

INVENTOR(S) : Fagan et al.

It is certified that error appears in the above-identified patent and that said Letters Patent is hereby corrected as shown below:

Column 4, line 44, please delete the word "districution", and substitute therefore the word --distribution--.

Column 7, line 58, after the word "is", please insert the word --to--.

Column 15, line 17, please delete the word "place" and substitute therefore the word --plate--.

Column 16, line 17, please delete the number "13B", and substitute therefore the number --138--.

Column 17, line 23, after the number "24a", please insert the words --of the --.

Column 17, line 43, please delete the word "describe", and substitute therefore the words --described herein, the distance--.

Column 17, line 47, please delete the word "on", and substitute therefore the word --one--.

Column 18, line 7, please delete the number "196", and substitute therefore the number --198--.

UNITED STATES PATENT AND TRADEMARK OFFICE
CERTIFICATE OF CORRECTION

PATENT NO. : 5,249,864
DATED : October 5, 1993
INVENTOR(S) : Fagan, et. al.

It is certified that error appears in the above-indentified patent and that said Letters Patent is hereby corrected as shown below:

Column 18, line 11, please delete the word "an", and substitute therefore the word --a--.

Signed and Sealed this

Nineteenth Day of July, 1994

Attest:

BRUCE LEHMAN

*Attesting Officer*   *Commissioner of Patents and Trademarks*